US007014867B2

(12) United States Patent
Fanara et al.

(10) Patent No.: US 7,014,867 B2
(45) Date of Patent: Mar. 21, 2006

(54) TABLET COMPRISING CETIRIZINE AND PSEUDOEPHEDRINE

(75) Inventors: Domenico Fanara, Wanze (BE); Anthony Guichaux, Fribourg (CH); Monique Berwaer, Ham-sur-Heure-Nalinnes (BE); Michel Deleers, Linkebeek (BE)

(73) Assignee: UCB Farchim SA, Bulle (CH)

( * ) Notice: Subject to any disclaimer, the term of this patent is extended or adjusted under 35 U.S.C. 154(b) by 0 days.

(21) Appl. No.: 10/481,264

(22) PCT Filed: Jun. 10, 2002

(86) PCT No.: PCT/EP02/06342

§ 371 (c)(1),
(2), (4) Date: Dec. 19, 2003

(87) PCT Pub. No.: WO03/002098

PCT Pub. Date: Jan. 9, 2003

(65) Prior Publication Data

US 2004/0170690 A1    Sep. 2, 2004

(30) Foreign Application Priority Data

Jun. 28, 2001  (EP) ................................. 01115807

(51) Int. Cl.
*A61K 9/24*    (2006.01)
*A61K 9/20*    (2006.01)
(52) U.S. Cl. ...................... 424/472; 424/464
(58) Field of Classification Search ............. 424/468, 424/472, 464
See application file for complete search history.

(56) References Cited

U.S. PATENT DOCUMENTS

| 5,876,752 | A | 3/1999 | Herbig et al. |
| 5,876,759 | A | 3/1999 | Gowan, Jr. |
| 6,027,746 | A | 2/2000 | Lech |
| 6,171,618 | B1 | 1/2001 | Johnson et al. |
| 6,267,986 | B1 * | 7/2001 | Jain et al. ................... 424/472 |
| 6,270,790 | B1 | 8/2001 | Robinson et al. |
| 6,469,009 | B1 | 10/2002 | Van De Venne et al. |
| 6,471,991 | B1 | 10/2002 | Robinson et al. |
| 6,489,329 | B1 | 12/2002 | Van de Venne et al. |
| 6,521,254 | B1 | 2/2003 | Weinstein et al. |
| 6,537,573 | B1 | 3/2003 | Johnson et al. |
| 6,569,463 | B1 | 5/2003 | Patel et al. |

FOREIGN PATENT DOCUMENTS

| EP | 0 811 374 | 12/1997 |
| EP | 0 997 143 | 5/2000 |
| EP | 1 241 110 | 9/2002 |
| WO | WO 88/08302 | 11/1988 |
| WO | WO 93/18757 | 3/1993 |
| WO | WO 97/04808 | 2/1997 |
| WO | 98 47794 | 9/1998 |
| WO | WO 98/41194 | 9/1998 |
| WO | WO 99/32125 | 7/1999 |
| WO | WO 01/21168 | 3/2001 |
| WO | WO 02/096392 | 12/2002 |

* cited by examiner

*Primary Examiner*—Thurman K. Page
*Assistant Examiner*—Humera N. Sheikh
(74) *Attorney, Agent, or Firm*—Wenderoth, Lind & Ponack, L.L.P.

(57) ABSTRACT

The present invention concerns a tablet comprising two distinct segments. More particularly, the invention relates to combinations of two pharmaceutical substances and methods of treatment of allergic disorders.

92 Claims, No Drawings

TABLET COMPRISING CETIRIZINE AND PSEUDOEPHEDRINE

This application is a 371 of PCT/EPO2/06342 filed Jun. 10, 2002, which claims benefit of Provisional Application 60/301,250 filed Jun. 28, 2001. This application claims foreign priority of European Application 01115807.8 filed Jun. 28, 2001.

The present invention concerns a tablet comprising two distinct segments. More particularly the invention relates to combinations of two pharmaceutical substances and methods of treatment of allergic disorders.

2-[2-[4-[(4-chlorophenyl)phenylmethyl]-1-piperazinyl] acetic acid, also known as cetirizine, and the dihydrochloride thereof are known by U.S. Pat. No. 4,525,358 which also discloses their antihistaminic properties. The compounds possess useful pharmacological properties. In particular, they are useful as antiallergic, antihistaminic, bronchodilatory and antispasmodic agents.

Some documents also disclose the use of specific stereoisomers of pharmaceutical substances for treating disorders in humans while avoiding adverse effects associated with the corresponding racemic mixture. In particular International Patent Applications published as WO 94/06429 and WO 94/06430 disclose methods of treating a condition caused by or contributed to by eosinophilia or enhanced eosinophil function in a human, which comprises administering to a human, in need of eosinophilic therapy, an amount of (+) cetirizine (respectively (−) cetirizine), or a pharmaceutically acceptable salt thereof, substantially free of its (−) stereoisomer (respectively its (+) stereoisomer), said amount being sufficient to alleviate said eosinophilia or enhanced eosinophil function but insufficient to cause said adverse effects.

On the other hand, a compound pseudoephedrine, is well known as sympathomimetic drug recognised as safe therapeutic agents effective in the relief of nasal congestion.

It is well known to those skilled in the art that combinations of pharmaceutical substances should always be handled with care because they are very susceptible of inducing unpredictable adverse effects in humans. In some cases, they also induce an efficiency of the treatment which is lower than that of each pharmaceutical substance taken alone.

In the treatment of allergic disorders such as for example a pollen associated allergic rhino-conjunctivitis, care should be taken, when combining an antihistaminic and a decongestant, not only to increase the overall efficiency of the treatment, i.e. the percentage of days during the whole treatment period, when the symptoms of sneezing, rhinorrhea, nasal obstruction, lacrimation, nasal and ocular pruritus are absent or at the most mild, but also to avoid possible adverse effects like insomnia and headache.

Several patent applications already disclosed binary and/or ternary combinations of pharmaceutical substances in specific amounts in view of treating various disorders in humans. In particular United Kingdom Patent 2 311 940 and European patent application 0 811 374 disclose a pharmaceutical composition comprising cetirizine and pseudoephedrine; U.S. Pat. No. 6,171,618 discloses a dosage form containing cetirizine as an immediate release component and pseudoephedrine as a controlled release component, a portion of the pseudoephedrine can be incorporated as an immediate release component.

In a more particular way, the international patent application WO 98/41194 discloses a pharmaceutical composition which can be administered orally, allowing the immediate release of a first active substance and the prolonged release of the same or of a second active substance, comprising A. at least one layer comprising an active substance and excipients which allow immediate release of the said active substance after administration, and
B. at least one second layer which allows the controlled release of the same or of a second active substance, this layer being a pharmaceutical composition comprising between 5 and 60% by weight, relative to the total weight of the composition, of at least one excipient, selected from inert matrices, hydrophilic matrices, lipid matrices, mixtures of inert matrices and of lipid matrices, mixtures of hydrophilic matrices and of inert matrices; and between 5 and 50% by weight, relative to the total weight of the composition, of at least one alkalinizing agent soluble in an aqueous phase under physiological pH conditions.

Due to the presence of the alkalinizing agent, this composition has demonstrated a good stability profile.

It has now surprisingly been found that such a pharmaceutical composition can be prepared by adding less than 5% of alkalinizing agent or in the absence of alkalinizing agent.

In such a way, it has been obtained a tablet having a specific release for a b.i.d. slow release (12 hours), although the pharmaceutical composition containing more than 5% of alkalizing agent exhibits a once a day release dosing.

Despite the fact that a lower amount of alkalinizing agent has been added, the tablet of the invention has also demonstrated a good stability profile.

Thus an objective of the present invention is to provide a useful combination of pharmaceutical substances for treating various disorders in humans, said combination being able to increase the efficiency of said treatment over the efficiency of each substance alone, while avoiding adverse effects during the said treatment.

Another objective of the present invention is to provide such a useful combination of pharmaceutical substances when the treatment in question is a therapy such as needed for rhinitis, cold, flu, cold-like and flulike symptoms.

The present invention encompasses a method of treating a disorder selected from rhinitis, cold, flu, cold-like and flu-like symptoms in a human, which comprises administering to a human in need of such therapy, a tablet comprising an effective amount of pseudoephedrine, an individual optical isomer or a pharmaceutically acceptable salt thereof and an effective amount of cetirizine, an individual optical isomer or a pharmaceutically acceptable salt thereof.

The term "a method for treating a disorder selected from rhinitis, cold, flu, cold-like and flu-like symptoms in a human" as used herein means providing relief from the symptoms of sneezing, rhinorrhea, nasal obstruction, nasal and ocular pruritus, lacrymation, and the like.

The term "pharmaceutically acceptable salts" as used herein with respect to cetirizine means not only their addition salts with non-toxic organic and inorganic acids, such as acetic, citric, succinic, ascorbic, hydrochloric, hydrobromic, sulfuric, and phosphoric acids and the like, but also their metal salts (for example sodium or potassium salts), ammonium salts, amine salts and aminoacid salts.

The term "pharmaceutically acceptable salt" as used herein with respect to pseudoephedrine means namely its hydrochloride and sulfate and equivalent non-toxic salts.

The term "individual optical isomer" as used herein means, when the molecule has a centre of asymmetry, the levorotatory and the dextrorotatary enantiomers thereof. As is well known in the art, purification of such enantiomers is a rather difficult process depending upon the selected way of preparation of the compound and the optical purity of the starting material. Therefore the term "individual optical isomer" as used herein means that the said compound comprises at least 90%, preferably at least 95%, by weight of the said individual (either dextro- or levorotatory) optical isomer and at most 10%, preferably at most 5%, by weight of the other individual (respectively levo- or dextrorotatary) optical isomer. Each individual optical isomer may be obtained from its racemic mixture by using conventional means such as disclosed in British patent application No. 2,225,321. Additionally, each individual optical isomer can be prepared from the racemic mixture by enzymatic biocatalytic resolution, such as disclosed in U.S. Pat. Nos. 4.800,162 and 5,057,427.

The preferred compounds for cetirizine are the racemate of 2-[2-[4-[(4-chlorophenyl)phenylmethyl]-1-piperazinyl]ethoxy]-acetic acid and its dihydrochloride salt which is well known as cetirizine dihydrochloride, and its levorotatory and dextrorotatory enantiomers (levocetirizine and dextrocetirizine).

In the present application the term "pseudoephedrine", used herein means pseudoephedrine itself, an individual optical isomer or a pharmaceutically acceptable salt thereof.

In the present application the term "cetirizine" means cetirizine itself (racemate of 2-[2-[4-[(4-chlorophenyl)phenylmethyl]-1-piperazinyl]ethoxy]-acetic acid), an individual optical isomer, any mixture of optical isomers, or a pharmaceutically acceptable salt thereof.

In a particular embodiment, the present invention concerns a tablet comprising at least two distinct segments, one segment of which comprises as active ingredient predominantly cetirizine and a second segment of which comprises as active ingredient predominantly pseudoephedrine, said segments being composed and formed in such a way that the resulting tablet is substantially free of impurities formed by reaction of cetirizine with pseudoephedrine and with the proviso that the tablet comprises less than 5% by weight, relative to the total weight of the tablet, of an alkalinizing agent.

In a second embodiment, the invention concerns a tablet comprising at least two distinct segments one segment of which comprises as active ingredient predominantly cetirizine and a second segment of which comprises as active ingredient predominantly pseudoephedrine, said segments being composed and formed in such a way that the pharmacokinetic profiles of the cetirizine and pseudoephedrine are substantially the same as in a dosage form containing each as sole active ingredient in the same amount.

By the term "segment" we understand a discrete volume of a pharmaceutical composition containing an active drug and one or more pharmaceutically acceptable excipients. A segment of a tablet may form, for example, a layer of a multilayer tablet (i.e. a layer of a bilayer tablet) or a core of a tablet or a coating fully or partially covering a core of a tablet. A segment may also be a particle fully or partially covered by a coating or a coating fully or partially covering a particle.

By "substantially free" we understand less than 5%, preferably less than 3% by weight. More preferably we understand less than 0.5%, further more less than 0.2% by weight.

Preferably, in the tablet according to the invention, the pseudoephedrine segment is substantially free of cetirizine, by which is meant less than 5%, preferably less than 3%, more preferably less than 0.5% of the cetirizine segment content in the pseudoephedrine segment. Preferably, in the tablet according to the invention, the cetirizine segment is substantially free of pseudoephedrine, by which is meant less than 5%, preferably less than 3%, more preferably less than 0.5% of the pseudoephedrine segment content in the cetirizine segment.

According to the invention, the interfacial surface area of the pseudoephedrine segment and cetirizine segment is less than 180 $mm^2$, and preferably from about 20 to about 150 $mm^2$. By interfacial area we understand the calculated contact surface between the two segments what ever the type of tablet (round, oblong, squared, caplet, . . . ) or the type of contact could be.

In another embodiment of the invention the tablet further comprises a barrier segment wherein said barrier segment separates the cetirizine segment and the pseudoephedrine segment. The barrier segment comprises materials known to persons skilled in the art.

In another embodiment of the invention, the pseudoephedrine segment comprises less than 5% by weight, relative to the total weight of the pseudoephedrine segment, of an alkalinizing agent.

The alkalinizing agent which can be used according to the present invention should preferably be soluble in the aqueous phase under physiological pH conditions. The alkalinizing agent may be chosen from alkali or alkaline-earth metal hydroxides, carbonates, bicarbonates and phosphates, sodium borate as well as basic salts of organic acids (example: sodium citrate). On the other hand, salts not soluble in water under physiological pH conditions, such as dibasic calcium phosphate, are not suitable according to the present invention.

In another embodiment of the invention, the tablet comprises a plurality of pseudoephedrine segments.

Preferably the cetirizine segment of the tablet is in the form of a compression coating or alternatively in the form of a spray coating. By the term "compression coating" we understand a small tablet utilised as part of the compression of a second tablet and where the small tablet is located almost in the centre and the rest of the powder compressed outside. By the term "spray coating" we understand an over coating of a tablet with the coating preparation containing an active substance.

Preferably the pseudoephedrine segment of the tablet contains inert pharmaceutical excipients in an amount of 0.75 to 4.5 times that of the pseudoephedrine itself by weight, and more preferably of 1 to 3 times.

Preferably the cetirizine segment of the tablet contains inert pharmaceutical excipients in an amount of 5 to 30 times that of the cetirizine itself by weight, and more preferably of 10 to 20 times.

Preferably the ratio of the total amount of inert pharmaceutical excipients present to the total aggregate amount of all active ingredients is between 2 and 6 by weight. The best results have been obtained with a ratio of about 3.

In the tablet according to the invention the weight ratio of pseudoephedrine to cetirizine is between 12 and 30. The best results have been obtained with a ratio of about 24.

In a preferred tablet the pseudoephedrine segment comprises about 108 to 132 mg and preferably 120 mg of pseudoephedrine and the cetirizine segment comprises about 4.5 to 5.5 mg and preferably 5 mg of cetirizine.

In a preferred embodiment of the invention the pseudoephedrine segment is a slow release formulation. By "slow release", we understand a release of 20 to 60% in 1 hour, and greater than 70% in 6 hours, or 40 to 80% in 2 hours, and greater than 70% in 6 hours in 500 ml water (HCl 0.1N) in USP apparatus 1 (37° C., 100 RPM).

In a preferred embodiment of the invention the cetirizine is in immediate release form. By "immediate release" we understand a release of more than 70% in 30 minutes, in 500 ml water (HCl 0.1N) in USP apparatus 1 (37° C., 100 RPM).

The tablet weight is between 200 to 800 mg, and preferably between 300 and 600 mg.

Preferably the tablet according to the invention comprises an amount of cetirizine which when dosed to a human subject gives a cetirizine area under the cetirizine plasma concentration versus time curve which is between 80% and 125% of the area under the cetirizine plasma concentration versus time curve observed when a dihydrochloride cetirizine immediate release tablet comprising said amount of cetirizine is dosed to same human subject at the same cetirizine dose.

Preferably the tablet according to the invention comprises an amount of pseudoephedrine which when dosed to a human subject gives a pseudoephedrine area under the pseudoephedrine plasma concentration versus time curve which is between 80% and 125% of the area under the pseudoephedrine plasma concentration versus time curve observed when a pseudoephedrine sustained release tablet comprising said amount of pseudoephedrine is dosed to same human subject.

Pseudoephedrine/cetirizine dosage forms of this invention provide pseudoephedrine and cetirizine blood or plasma levels which are equivalent to those resulting from dosing separate pseudoephedrine and cetirizine control formulation.

An appropriate 120 mg pseudoephedrine control formulation is the product sold under the tradename SUDAFED 12 hr tablets (Warner-Lambert Consumer Products; described in 2001 Physician's Desk Reference). An appropriate cetirizine control formulation is a 5 mg immediate release cetirizine (ZYRTEC®) sold by UCB, S.A. and PFIZER.

To test in vivo equivalence, the following test is carried out. A group of at least 12 healthy human subjects is divided into 2 groups. One group is orally dosed the pseudoephedrine/cetirizine dosage form of this invention and the other group is dosed a SUDAFED 12 hr 120 mg caplet (or equivalent) and a 5 mg product sold under the tradename ZYRTEC tablet. Blood is collected from the subjects at regular timings after dosing and plasma is prepared.

An HPLC or LC/MS or LC/MS/MS assay is used to determine the concentration of pseudoephedrine and cetirizine in each sample.

After about one week the subjects who originally received the pseudoephedrine/cetirizine dosage form are now dosed with the pseudoephedrine control and the cetirizine control. The subjects who originally received the pseudoephedrine control and cetirizine control are now dosed with the pseudoephedrine/cetirizine combination dosage form. Plasma concentrations of pseudoephedrine and cetirizine are measured. For each subject, the plasma pseudoephedrine vs. time plot is prepared, and the plasma cetirizine vs. time plot is prepared.

The cetirizine CMAX is the maximum cetirizine plasma concentration. The cetirizine CMAX for the combination dosage form is divided by the CMAX for the immediate release cetirizine control, for each subject, and the average CMAX ratio is determined. Pseudoephedrine/cetirizine dosage forms of this invention give an average CMAX ratio between 0.8 and 1.25.

The area under the plasma cetirizine concentration vs. time curve (AUC) is determined for the combination dosage form and the cetirizine control tablet. The cetirizine AUC for the combination dosage form is divided by the cetirizine AUC for the immediate release cetirizine control, for each subject, and the average AUC ratio is determined.

Pseudoephedrine/cetirizine average dosage forms of this invention give an average AUC ratio between 0.8 and 1.25, and in addition, the 90% confidence intervals are between 0.8 and 1.25.

The average AUC ratio for pseudoephedrine is similarly obtained. Pseudoephedrine/cetirizine dosage forms of this invention give an average pseudoephedrine AUC ratio between 0.8 and 1.25, and in addition, the 90% confidence intervals are between 0.8 and 1.25.

The plasma analysis of cetirizine and pseudoephedrine is as follows. Blood sufficient to provide a minimum of 5 ml plasma (two portions of 2.5 ml) for analysis of cetirizine and pseudoephedrine pharmacokinetics will be collected in heparinized tubes at the following times: 0 (Oust prior to dosing), 0.5, 1,2,3,4,6,8,10, 12, 16,24, 36,and 48 hours after dose. At the discretion of the investigator, subjects may be discharged after the 12-hour sample on days 9 and 25. Samples will be centrifuged at approximately 4° C. and the plasma will be stored in appropriately labeled; screw-capped polypropylene tubes at −20° C. within 1 hour of collection. Samples from each individual subject will be stored as a package for that subject.

AUC represents the area under the curve, Cmax represents the maximum concentration detected and $T_{max}$ represents the time necessary to obtain Cmax.

In the tablet according to the invention the particle size of the pseudoephedrine present is chosen such that it has a flow index less than 25. By "flow index" we understand the flowability index corresponding to the diameter of the smallest hole through which sample will pass three tests out of three (equipment from Hanson Research Corporation Chatsworth).

The particle size determination is carried out by means of airjet sifting under the following conditions: individual sieves according to ASTM E11, 10 g of substance, the equipment used is the Alpine airjet sieve, a low pressure is used, preferably 250 mm $H_2O$ (between 100–300 mm $H_2O$), the sieving period is 5 minutes, and the auxiliary is 0.30 g antistatic per 10 g substance and preferably Aerosil R 972 (Degussa).

In the tablet according to the invention the particle size of the pseudoephedrine present is chosen such that it has an ability to settle of less than 30 mil. The ability to settle ($V_{10}$–$V_{500}$) is measured according to Eur. Pharm. 2.9.15.

Preferably in the tablet according to the invention not more than 10% of the pseudoephedrine present therein has a particle size of less than 100 μm. More preferably the particle size of the pseudoephedrine is such that at least 95% of the particles are less than 500 μm and not more than 15% are less than 106 μm.

The best results have been obtained with a tablet wherein the pseudoephedrine is crystalline.

The tablet according to a preferred embodiment of the invention comprises, as hydrophilic polymer, a methyl cellulose ether derivative and preferably a substituted hydroxylated methyl cellulose.

The viscosity of the methyl cellulose ether derivative is measured according to Eur. Pharm. described method in cellulose derivatives monographs or according to USP method n° <911>.

The best results have been obtained with the product sold under the trademark Methocel K15 MCR which is an hydroxypropylmethylcellulose (methoxyl: 19–24%, hydroxypropyl: 7–12%), chlorides: max 0.5%; having an apparent viscosity of 11000 to 21000 mPa (=cP) and a particle size: min 90%<100 mesh.

Preferably the ratio of hydroxypropylmethylcellulose (HPMC) to the pseudoephedrine is between 0.5 to 2 by weight.

In the tablet according to a preferred embodiment of the invention the cetirizine containing segment also contains a disintegrant, preferably in the range less than 5% by weight of cetirizine segment and most preferably in the range of 1 to 5%. Examples of suitable disintegrant are sodium starch glycolate, sodium crosscarmelose (cross-linked carboxy methyl cellulose), polyvinylpyrrolidone derivatives, crospovidone (polyplasdone XL, PLP XL). The best results have been obtained with a disintegrant being a cross-linked carboxy methyl cellulose.

In a preferred embodiment of the tablet the cetirizine segment contains excipients including a polyhydroxyl compound having a molecular weight of less than 400. Preferably the polyhydroxyl compound is a sugar. Most preferably the sugar is lactose.

A more preferred embodiment of the invention is the tablet which is a bi-layer tablet, the cetirizine segment being a layer and the pseudoephedrine segment being a layer. Preferably the weight ratio of the pseudoephedrine layer to the cetirizine layer is between 0.25 to 10, and most preferably between 2 and 6.

In the preferred embodiment the outer face of each of the two layers has a different shape. Preferably the tablet has a first face which is the pseudoephedrine layer, having multiple radii of curvature, and most preferably three. Preferably the tablet has a second face which is the cetirizine layer, having a single radius of curvature. Radius of curvature is defined in American Pharmaceutical Association Tableting Specification Manual, 4$^{th}$ edition, 2215 Constitution Avenue, NW, Washington. D.C. 20037-2985, pp 45 and 46); cup radius is a single arc generated from the tablet's centerline (midpoint) across the tablet's diameter, minor axis or major axis; the cup radius forme the cup's profile; cup is the depression, or concavity, at the end of a punch tip; Major axis: length of a shaped tablet, minor axis is width of a shaped tablet.

A tablet may comprises an additional coating layer. In an alternative the coating layer can acted as a taste masking agent. Examples of suitable taste masking agents are cellulose derivatives (methyl-, carboxymethyl-hydroxymethyl-, hydroxy ethyl-, hydroxymethylpropyl, cellulose) vinyl derivatives(polyvinyl alcohol, polyvinyl acetate), acrylic and methacrylic derivatives (Eudragits®), maleic copolymers, polyoxyethylene glycols, natural resins (zeine, gums).

A tablet may also contain some pharmaceutically acceptable fillers as excipients. Examples of suitable fillers are starch and derivatives, lactose, mannitol, sucrose, glucose, sorbitol, calcium phosphates, maltodextrines, polyvinylpyrrolidone, polyethylene glycols, microcrystalline cellulose, organic acids.

In a preferred embodiment of the invention the tablet is packaged in a moisture and oxygen protective packaging material.

In a tablet according to a preferred embodiment of the invention, the pseudoephedrine segment comprises at least one excipient, selected from inert matrices, hydrophilic matrices, lipid matrices, mixtures of inert matrices and of lipid matrices, mixtures of hydrophilic matrices and of lipid matrices, mixtures of hydrophilic matrices and of inert matrices.

The tablets according to a preferred embodiment of the present invention comprise matrix excipients chosen from inert, hydrophilic and lipophilic matrices.

Examples of inert matrices which can be used according to the present invention are: polyvinyl chloride, polyethylene, vinyl acetate/vinyl chloride copolymers, polymethylmethacrylates, polyamides, silicones, ethyl cellulose, polystyrene and the like.

Examples of hydrophilic matrices which can be used according to the present invention are cellulose derivatives (hydroxypropyl methylcellulose, hydroxyethyl cellulose, hydroxypropyl cellulose, methylcellulose and the like), non-cellulose polysaccharides (galacto-mannans, guar gum, carob gum, gum arabic, sterculia gum, agar, alginates and the like) and acrylic acid polymers (carbopols 934P and 974P and the like). The hydrophilic matrices preferably used according to the present invention are hydroxypropyl methyl celluloses, such as compounds sold under the trademark METHOCEL K or E.

Examples of lipid matrices which can be used according to the present invention are glycerides (mono-, di- or triglycerides: stearin, palmitin, laurin, myristin, hydrogenated castor or cottonseed oils, precirol and the like), fatty acids and alcohols (stearic acid, palmitic acid, lauric acid; stearyl alcohol, cetyl alcohol, cetostearyl alcohols, and the like), fatty acid esters (monostearates of propylene glycol and of sucrose, sucrose distearate and the like) and waxes (white wax, cachalot wax and the like).

In addition to the above-mentioned components, the tablet according to the present invention may also contain other excipients such as diluents (example: Emcompress, lactose and the like), binders (Avicel, starches, polyvinylpyrrolidone and the like), disintegrants (starches and modified starches, cellulose derivatives, alginic derivatives, pectins and the like), lubricants (talc, magnesium stearate, colloidal silica and the like), taste-masking agents (α-cyclodextrin, β-cyclodextrin, γ-cyclodextrin and their alkylated derivatives), flavourings or colourings as well as coating agents (example: cellulose derivatives, methacrylic resins, polyvinyl chloride, nylons and the like).

For implementing the method of treatment of the invention the tablet hereinabove described should contain an effective amount of cetirizine and pseudoephedrine. An effective amount can be readily determined by the use of conventional techniques and by observing results obtained under analogous circumstance. In determining the effective amount, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

Additionally, the respective proportions of cetirizine and pseudoephedrine in the tablet should preferably be such that the said tablet comprises about 0.25 to about 2.5 percent by weight of cetirizine and about 10 to about 45 percent by weight of pseudoephedrine.

A tablet according to the invention can be administered to a patient in any form or mode which makes the tablet bioavailable in effective amounts, namely the oral route. One skilled in the art of preparing formulations can readily select the proper form and mode of administration depending upon the particular characteristics of the disease state to be treated, the stage of the disease, and other relevant circumstances.

The tablets of the invention can comprise at least one pharmaceutically acceptable excipient, the proportion and nature of which are determined by the solubility and chemical properties of the tablet selected, the chosen route of administration, and standard pharmaceutical practice.

More particularly, the present invention contemplates pharmaceutical compositions consisting essentially of a therapeutically effective amount of the above-described active compounds in association with one or more pharmaceutically acceptable excipients.

The excipient material may be a solid or semi-solid material which can serve as a vehicle or medium for the active ingredient. Suitable excipient materials are well known in the art. The pharmaceutical tablets of the invention may be adapted for oral use and may be administered to the patient in the form of tablets, or capsules.

The excipient material should be suitably selected with respect to the intended form of administration, and consistent with conventional pharmaceutical practice. For instance, for oral administration in the form of tablets or capsules, the therapeutically active drug components may be combined with any oral non-toxic pharmaceutically acceptable inert excipient such as lactose or starch. Optionally, the pharmaceutical tablet of the invention also contain a binder such as microcrystalline cellulose, gum tragacanth or gelatine, a disintegrating agent such as alginic acid, a lubricant such as magnesium stearate, a glidant such as colloidal silicon dioxide, a sweetening agent such as sucrose or saccharin, a coloring agent or a flavouring agent such as peppermint or methyl salicylate Because of their easy administration, tablets represent the most advantageous oral dosage unit form. If desired, tablets may be coated by standard aqueous or nonaqueous techniques with sugar, shellac or other entering coating agents. Desirably, each tablet or capsule contains from about 15 mg to about 300 mg of the active ingredients.

A tablet according to the invention can be prepared according to various methods known to persons skilled in the art.

The present invention concerns also the use of a tablet described, for the manufacture of a medicament for preventing or treating disorders or conditions associated with rhinitis, cold, flu, cold-like and flu-like symptoms and allergic rhinitis, relief of nasal congestion, seasonal rhinitis, sneezing, rhinorrhea, nasal and ocular pruritus, redness of the eyes, tearing, sneezing.

The present invention concerns also a method for preventing or treating in humans and mammals disorders or conditions associated with rhinitis, cold, flu, cold-like and flu-like symptoms and allergic rhinitis, relief of nasal congestion, seasonal rhinitis, sneezing, rhinorrhea, nasal and ocular pruritus, redness of the eyes, tearing, sneezing.

The invention is further defined by reference to the following examples describing in detail the tablets of the present invention, as well as their utility.

EXAMPLES

Example 1

Composition of the Pseudoephedrine Slow Release Segment of the Bi-Layer Tablets

A phase one, opened, randomised pilot study compared the oral bioavailability of experimental 120 mg sustained release segment pseudoephedrine formulations (table 1).

TABLE 1

Composition of tablets A and B.

| Components | mg/tablet A | mg/tablet B |
|---|---|---|
| Pseudoephedrine.HCl | 120 | 120 |
| HPMC (a) | — | 120 |
| HPMC (b) | 200 | — |
| Microcrystalline cellulose | 74 | 55.5 |
| Colloidal silicon dioxide | 2 | 1.5 |
| Magnesium stearate | 4 | 3 |

HPMC (a) represents a compound hydroxypropyl methylcellulose having an apparent viscosity of 11250 to 21000 mPA (=cP (centipoises)), as defined in USP monograph hydroxypropyl methylcellulose.
HPMC (b) represents a compound hydroxypropyl methylcellulose having an apparent viscosity of 80000 to 120000 mPa (=cP).

The objective was to compare the oral bioavailability of the experimental sustained release formulations and an immediate release reference tablet (60 mg) given twice a day in 8 healthy male subjects.

The main pharmacokinetic parameters are listed in table 2.

TABLE 2

Main pharmacokinetic parameters after oral administration of 120 mg of pseudoephedrine in 8 healthy volunteers

| Treatment | Reference | A | B |
|---|---|---|---|
| $C_{max}$ (ng/mL) | 391 | 259 | 295 |
| $t_{max}$ (h) | 1.5 | 5 | 5 |
| AUC (ng · h/mL) | 3877 | 3943 | 4249 |

The two experimental formulations (A and B), which showed a clear slow release profile, were bioequivalent to the reference formulation.

The B formulation was chosen for further development as pseudoephedrine layer given its longer plateau time in the curve compared to formulation A.

Example 2

Dissolution Profile's pH Dependence for Tablet B Segment

Dissolution profile of pseudoephedrine is assessed at various pHs (water, HCl=0.1 N, pH=4.5, 6.8 and 7.5, USP 24 Apparatus 1, 100 rpm, 37° C.). Results are expressed in table 3.

TABLE 3

In vitro dissolution data of tablet B segment at various pHs.

| Time (h) | Water | HCl 0.1 N | pH 4.5 | pH 6.8 | pH 7.5 |
|---|---|---|---|---|---|
| 0 | — | — | — | — | — |
| 1 | 44.1 | 39.4 | 39.6 | 40.4 | 41.4 |
| 2 | 62.1 | 57.0 | 58.0 | 58.2 | 59.4 |
| 3 | 74.9 | 68.5 | 70.1 | 70.8 | 70.5 |
| 4 | 84.0 | 77.9 | 79.0 | 79.6 | 79.2 |
| 6 | 92.7 | 89.3 | 92.3 | 90.8 | 90.6 |
| 8 | 97.8 | 97.3 | 96.7 | 96.7 | 96.2 |
| 12 | — | 105.3 | 101.2 | 100.9 | 99.9 |

The results show a pH-independent in vitro dissolution.

Example 3

In vitro Dissolution of a Cetirizine.HCl/pseudoephedrine.HCl 5mg/120 mg Bi-layer Tablet Coated cetirizine.HCl/pseudoephedrine.HCl bi-layer tablets were prepared.

The particle size of the pseudoephedrine is such that at least 95% of the particles are less than 500 μm and not more than 15% are less than 106 μm.

The formulation of these tablets is presented in table 4.

TABLE 4

Composition of 5 mg/120 mg film coated cetirizine.HCl/pseudoephedrine.HCl tablets

| | | mg/tablet |
|---|---|---|
| Core's first layer: | Pseudoephedrine.HCl | 120 |
| | HPMC (a) | 120 |
| | Microcrystalline cellulose | 57 |
| | Colloidal silicon dioxide | 1.5 |
| | Magnesium stearate | 1.5 |
| Core's second layer: | Cetirizine.HCl | 5 |
| | Lactose monohydrate | 43.23 |
| | Microcrystalline cellulose | 19.15 |
| | Croscarmellose sodium | 1.40 |
| | Colloidal silicon dioxide | 0.52 |
| | Magnesium stearate | 0.70 |
| Coating material: | Opadry white | 11.10 |

The product Opadry white is a combination of polymers for the aqueous film coating (hydroxypropylmethylcellulose, titanium dioxide, polyethylene glycol 400).

The components of each core layer are mixed separately an then compressed in a bi-layer rotary tablet press. Then the tablets are coated with Opadry.

The tablet has a first face, which is the pseudoephedrine layer, having multiple radii of curvature. The tablet has a second face, which is the cetirizine layer, having a single radius of curvature.

The interfacial surface area of the pseudoephedrine segment and cetirizine segment is about 78.5 mm$^2$. The diameter of the tablet is about 10 mm.

The tablet is packaged in a moisture and oxygen protective packaging material.

Dissolution profiles of pseudoephedrine and cetirizine are assessed with the method described in example 2 (medium HCl=0.1 N). The results are expressed in table 5.

TABLE 5

In vitro dissolution data of a 5 mg/120 mg film coated cetirizine.HCl/pseudoephedrine.HCl bi-layer tablet.

| | Percentage of dissolved drug | |
|---|---|---|
| Time(h) | Pseudoephedrine.HCl | Cetirizine.HCl |
| 0.25 | 16 | 88 |
| 0.50 | 26 | 94 |
| 0.75 | 33 | 95 |
| 1 | 40 | 97 |
| 4 | 81 | 99 |
| 8 | 97 | 99 |
| 12 | 100 | 99 |

The results show the slow release of pseudoephedrine.HCl (similar to the results of example 2) and the immediate release of cetirizine.HCl.

The dissolution test is made in an USP Apparatus 1, volume 500 ml, speed 100 rpm, 37° C.

A stability test shows that the cetirizine segment is substantially free of pseudoephedrine, and that pseudoephedrine segment is substantially free of cetirizine (less than 0.2% by weight).

The invention claimed is:

1. A tablet comprising at least two distinct segments, one segment of which comprises as active ingredient predominantly cetirizine and a second segment of which comprises as active ingredient predominantly pseudoephedrine, said segments being composed and formed in such a way that the resulting tablet is substantially free of impurities formed by reaction of cetirizine with pseudoephedrine, wherein the interfacial surface area of the pseudoephedrine segment and cetirizine segment is less than 180 mm$^2$ and with the proviso that the tablet comprises less than 5% by weight, relative to the total weight of the tablet, of an alkalinizing agent.

2. A tablet according to claim 1 wherein the pseudoephedrine segment is substantially free of cetirizine.

3. A tablet according to claim 1 wherein the cetirizine segment is substantially free of pseudoephedrine.

4. A tablet according to claim 1 wherein the tablet further comprises a barrier segment wherein said barrier segment separates the cetirizine segment and the pseudoephedrine segment.

5. A tablet according to claim 1 wherein the pseudoephedrine segment comprises less than 5% by weight, relative to the total weight of the pseudoephedrine segment, of an alkalinizing agent.

6. A tablet according to claim 1 wherein the tablet comprises a plurality of pseudoephedrine segments.

7. A tablet according to claim 1 wherein said cetirizine segment is in the form of a compression coating.

8. A tablet according to claim 1 wherein said cetirizine segment is in the form of a spray coating.

9. A tablet according to claim 1 wherein the pseudoephedrine segment contains inert pharmaceutical excipients in an amount of 0.75 to 4.5 times that of the pseudoephedrine itself by weight.

10. A tablet according to claim 1 wherein the cetirizine segment contains inert pharmaceutical excipients in an amount of 5 to 30 times that of the cetirizine itself by weight.

11. A tablet according to claim 1 wherein the ratio of the total amount of inert pharmaceutical excipients present to the total aggregate amount of all active ingredients is between 2 and 6 by weight.

12. A tablet according to claim 1 wherein the weight ratio of pseudoephedrine to cetirizine is between 12 and 30.

13. A tablet according to claim 12 wherein the weight ratio of pseudoephedrine to cetirizine is about 24.

14. A tablet according to claim 1 wherein the pseudoephedrine segment comprises between about 108 and 132 mg of pseudoephedrine and the cetirizine segment comprises between about 4.5 and 5.5 mg of cetirizine.

15. A tablet according to claim 1 wherein the pseudoephedrine segment is in a slow release form.

16. A tablet according to claim 1 wherein the cetirizine is in an immediate release form.

17. A tablet according to claim 1 wherein the tablet weight is between 200 to 800 mg.

18. A tablet according to claim 1 wherein the tablet comprises an amount of cetirizine which when dosed to a human subject gives a cetirizine area under the plasma cetirizine concentration versus time curve which is between 80% and 125% of the area under the plasma cetirizine concentration versus time curve observed when a dihydrochloride cetirizine immediate release tablet comprising said amount of cetirizine is dosed to same human subject at the same cetirizine dose.

19. A tablet according to claim 1 wherein the tablet comprises an amount of pseudoephedrine which when dosed to a human subject gives a pseudoephedrine area under the pseudoephedrine plasma concentration versus time curve which is between 80% and 125% of the area under the plasma pseudoephedrine concentration versus time curve observed when a pseudoephedrine sustained release tablet comprising said amount of pseudoephedrine is dosed to same human subject.

20. A tablet according to claim 1 wherein the particle size of the pseudoephedrine present is chosen such that it has a flow index less than 25.

21. A tablet according to claim 1 wherein the particle size of the pseudoephedrine present is chosen such that it has an ability to settle of less than 30 ml.

22. A tablet according to claim 1 wherein not more than 10% of the pseudoephedrine present therein has a particle size of less than 100 µm.

23. A tablet according to claim 21 wherein the particle size of the pseudoephedrine is such that at least 95% of the particles are less than 500 µm and not more than 15% are less than 106 µm.

24. A tablet according to claim 21 wherein the pseudoephedrine is crystalline.

25. A tablet according to claim 1 wherein the pseudoephedrine containing segment also contains a methyl cellulose ether derivative having a viscosity of about 11,000 to 21,000 mPa.

26. A tablet according to claim 25 wherein the methyl cellulose ether derivative is a substituted hydroxylated methyl cellulose.

27. A tablet according to claim 25 wherein the methyl cellulose ether derivative is an hydroxypropylmethylcellulose.

28. A tablet according to claim 27 wherein the derivative is an hydroxypropylmethylcellulose (methoxyl: 19–24%, hydroxypropyl: 7–12%), chlorides: max 0.5%; having an apparent viscosity of 11250 to 21000 mPa and a particle size: min 90%<100 mesh.

29. A tablet according to claim 25 wherein the ratio of hydroxypropylmethylcellulose (HPMC) to the pseudoephedrine is between 0.5 to 2 by weight.

30. A tablet according to claim 1 wherein the cetirizine containing segment also contains a disintegrant.

31. A tablet according to claim 30 wherein the cetirizine containing segment also contains a disintegrant in the range less than 5% by weight of cetirizine segment.

32. A tablet according to claim 30 wherein the disintegrant is a cross-linked carboxy methyl cellulose.

33. A tablet according to claim 1 wherein the cetirizine segment contains excipients including a polyhydroxyl compound having a molecular weight of less than 400.

34. A tablet according to claim 33 wherein the polyhydroxyl compound is a sugar.

35. A tablet according to claim 34 wherein the sugar is lactose.

36. A tablet according to claim 1 wherein the tablet is a bi-layer tablet, the cetirizine segment being a layer and the pseudoephedrine segment being a layer.

37. A tablet according to claim 36 wherein the weight ratio of the pseudoephedrine layer to the cetirizine layer is between 0.25 to 10.

38. A tablet according to claim 36 wherein the outer face of each of the two layers has a different shape.

39. A tablet according to claim 38 wherein the tablet has a first face which is the pseudoephedrine layer, having multiple radii of curvature.

40. A tablet according to claim 38 wherein the tablet has a second face which is the cetirizine layer, having a single radius of curvature.

41. A tablet according to claim 1 which comprises an additional coating layer.

42. A tablet according to claim 41 wherein the coating layer can act as a taste masking agent.

43. A tablet according to claim 1 wherein the tablet is packaged in a moisture protective packaging material.

44. A tablet according to claim 1 wherein the tablet is packaged in an oxygen protective packaging material.

45. A tablet according to claim 1 wherein the cetirizine segment comprises cetirizine dihydrochloride.

46. A tablet according to claim 1 wherein the cetirizine segment comprises levocetirizine.

47. A tablet comprising at least two distinct segments, one segment of which comprises as active ingredient predominantly cetirizine and a second segment of which comprises as active ingredient predominantly pseudoephedrine, wherein the interfacial surface area of the pseudoephedrine segment and cetirizine segment is less than 180 mm$^2$, said segments being composed and formed in such a way that the pharmacokinetic profiles of the cetirizine and pseudoephedrine are substantially the same as in a dosage form containing each as sole active ingredient in the same amount.

48. A tablet according to claim 47 wherein the pseudoephedrine segment is substantially free of cetirizine.

49. A tablet according to claim 47 wherein the cetirizine segment is substantially free of pseudoephedrine.

50. A tablet according to claim 47 wherein the tablet further comprises a barrier segment wherein said barrier segment separates the cetirizine segment and the pseudoephedrine segment.

51. A tablet according to claim 47 wherein the pseudoephedrine segment comprises less than 5% by weight, relative to the total weight of the pseudoephedrine segment, of an alkalinizing agent.

52. A tablet according to claim 47 wherein the tablet comprises a plurality of pseudoephedrine segments.

53. A tablet according to claim 47 wherein said cetirizine segment is in the form of a compression coating.

54. A tablet according to claim 47 wherein said cetirizine segment is in the form of a spray coating.

55. A tablet according to claim 47 wherein the pseudoephedrine segment contains inert pharmaceutical excipients in an amount of 0.75 to 4.5 times that of the pseudoephedrine itself by weight.

56. A tablet according to claim 47 wherein the cetirizine segment contains inert pharmaceutical excipients in an amount of 5 to 30 times that of the cetirizine itself by weight.

57. A tablet according to claim 47 wherein the ratio of the total amount of inert pharmaceutical excipients present to the total aggregate amount of all active ingredients is between 2 and 6 by weight.

58. A tablet according to claim 47 wherein the weight ratio of pseudoephedrine to cetirizine is between 12 and 30.

59. A tablet according to claim 58 wherein the weight ratio of pseudoephedrine to cetirizine is about 24.

60. A tablet according to claim 47 wherein the pseudoephedrine segment comprises between about 108 and 132 mg of pseudoephedrine and the cetirizine segment comprises between about 4.5 and 5.5 mg of cetirizine.

61. A tablet according to claim 47 wherein the pseudoephedrine segment is in a slow release form.

62. A tablet according to claim 47 wherein the cetirizine is in an immediate release form.

63. A tablet according to claim 47 wherein the tablet weight is between 200 to 800 mg.

64. A tablet according to claim 47 wherein the tablet comprises an amount of cetirizine which when dosed to a human subject gives a cetirizine area under the plasma cetirizine concentration versus time curve which is between 80% and 125% of the area under the plasma cetirizine concentration versus time curve observed when a dihydrochloride cetirizine immediate release tablet comprising said amount of cetirizine is dosed to same human subject at the same cetirizine dose.

65. A tablet according to claim 47 wherein the tablet comprises an amount of pseudoephedrine which when dosed to a human subject gives a pseudoephedrine area under the pseudoephedrine plasma concentration versus time curve which is between 80% and 125% of the area under the plasma pseudoephedrine concentration versus time curve observed when a pseudoephedrine sustained release tablet comprising said amount of pseudoephedrine is dosed to same human subject.

66. A tablet according to claim 47 wherein the particle size of the pseudoephedrine present is chosen such that it has a flow index less than 25.

67. A tablet according to claim 47 wherein the particle size of the pseudoephedrine present is chosen such that it has an ability to settle of less than 30 ml.

68. A tablet according to claim 47 wherein not more than 10% of the pseudoephedrine present therein has a particle size of less than 100 $\mu$m.

69. A tablet according to claim 67 wherein the particle size of the pseudoephedrine is such that at least 95% of the particles are less than 500 $\mu$m and not more than 15% are less than 106 $\mu$m.

70. A tablet according to claim 67 wherein the pseudoephedrine is crystalline.

71. A tablet according to claim 47 wherein the pseudoephedrine containing segment also contains a methyl cellulose ether derivative having a viscosity of about 11,000 to 21,000 mPa.

72. A tablet according to claim 71 wherein the methyl cellulose ether derivative is a substituted hydroxylated methyl cellulose.

73. A tablet according to claim 71 wherein the methyl cellulose ether derivative is an hydroxypropylmethylcellulose.

74. A tablet according to claim 73 wherein the derivative is an hydroxypropylmethylcellulose (methoxyl: 19–24%, hydroxypropyl: 7–12%), chlorides: max 0.5%; having an apparent viscosity of 11250 to 21000 mPa and a particle size: min 90%<100 mesh.

75. A tablet according to claim 71 wherein the ratio of hydroxypropylmethylcellulose (HPMC) to the pseudoephedrine is between 0.5 to 2 by weight.

76. A tablet according to claim 47 wherein the cetirizine containing segment also contains a disintegrant.

77. A tablet according to claim 76 wherein the cetirizine containing segment also contains a disintegrant in the range less than 5% by weight of cetirizine segment.

78. A tablet according to claim 76 wherein the disintegrant is a cross-linked carboxy methyl cellulose.

79. A tablet according to claim 47 wherein the cetirizine segment contains excipients including a polyhydroxyl compound having a molecular weight of less than 400.

80. A tablet according to claim 79 wherein the polyhydroxyl compound is a sugar.

81. A tablet according to claim 80 wherein the sugar is lactose.

82. A tablet according to claim 47 wherein the tablet is a bi-layer tablet, the cetirizine segment being a layer and the pseudoephedrine segment being a layer.

83. A tablet according to claim 82 wherein the weight ratio of the pseudoephedrine layer to the cetirizine layer is between 0.25 to 10.

84. A tablet according to claim 82 wherein the outer face of each of the two layers has a different shape.

85. A tablet according to claim 84 wherein the tablet has a first face which is the pseudoephedrine layer, having multiple radii of curvature.

86. A tablet according to claim 84 wherein the tablet has a second face which is the cetirizine layer, having a single radius of curvature.

87. A tablet according to claim 47 which comprises an additional coating layer.

88. A tablet according to claim 87 wherein the coating layer can act as a taste masking agent.

89. A tablet according to claim 47 wherein the tablet is packaged in a moisture protective packaging material.

90. A tablet according to claim 47 wherein the tablet is packaged in an oxygen protective packaging material.

91. A tablet according to claim 47 wherein the cetirizine segment comprises cetirizine dihydrochloride.

92. A tablet according to claim 47 wherein the cetirizine segment comprises levocetirizine.

* * * * *